(12) United States Patent
Chelyapov et al.

(10) Patent No.: US 10,760,054 B2
(45) Date of Patent: Sep. 1, 2020

(54) NATURAL KILLER CELLS AND METHODS FOR ENHANCING VIABILITY, PROLIFERATION AND CYTOTOXICITY OF SAME FOLLOWING CRYOPRESERVATION

(71) Applicant: RESTEM LLC, Miami, FL (US)

(72) Inventors: Nickolas Chelyapov, Newport Beach, CA (US); Rafael Gonzalez, Placentia, CA (US)

(73) Assignee: RESTEM LLC DE (US)

( * ) Notice: Subject to any disclaimer, the term of this patent is extended or adjusted under 35 U.S.C. 154(b) by 775 days.

(21) Appl. No.: 14/847,982

(22) Filed: Sep. 8, 2015

(65) Prior Publication Data

US 2016/0186138 A1    Jun. 30, 2016

Related U.S. Application Data

(60) Provisional application No. 62/097,535, filed on Dec. 29, 2014.

(51) Int. Cl.
*C12N 5/0783* (2010.01)
*C07H 21/00* (2006.01)

(52) U.S. Cl.
CPC ........ *C12N 5/0646* (2013.01); *C12N 2500/40* (2013.01); *C12N 2501/20* (2013.01)

(58) Field of Classification Search
None
See application file for complete search history.

(56) References Cited

U.S. PATENT DOCUMENTS

| 8,735,148 | B2 | 5/2014 | Lowdell |
| 2001/0034330 | A1 | 10/2001 | Kensil |
| 2012/0308986 | A1 | 12/2012 | Deng |
| 2013/0295671 | A1 | 11/2013 | Deng |
| 2014/0143268 | A1 | 5/2014 | Finkelstein et al. |
| 2015/0037887 | A1 | 2/2015 | Deng |
| 2016/0075996 | A1 | 3/2016 | Terunuma |

OTHER PUBLICATIONS

Kawai et al (Transfusion, 1988, 28(6): 531-535) (Year: 1998).*
Yang et al (Intern. Immunopharm. Jan. 2013, 15(1): 89-96) (Year: 2013).*
Berg et al (Cytotherapy 2009, 11(3): 341-355) (Year: 2009).*
Xuewen Deng et al., Synergystic cytotoxicity of ex vivo expanded natural killer cells in combination with monoclonocal antibody drugs against cancer cells, International Immunopharmacology, 14(2012) 593-605, Elsevier.

* cited by examiner

*Primary Examiner* — G. R. Ewoldt
*Assistant Examiner* — Marianne DiBrino
(74) *Attorney, Agent, or Firm* — Law Office of Darius Gleason APC (57) ABSTRACT

The invention provides compositions and methods of culturing Natural Killer Cells that increase viability, proliferation and cytotoxicity following cryopreservation.

16 Claims, 4 Drawing Sheets

Specification includes a Sequence Listing.

SEQUENCE LISTING

```
<160> NUMBER OF SEQ ID NOS: 9

<210> SEQ ID NO 1
<211> LENGTH: 29
<212> TYPE: DNA
<213> ORGANISM: Artificial Sequence
<220> FEATURE:
<223> OTHER INFORMATION: Synthetic Oligodeoxyribonucleotide

<400> SEQUENCE: 1
tcgcgaacgt tcgccgcgtt cgaacgcgg                                         29

<210> SEQ ID NO 2
<211> LENGTH: 72
```

```
<212> TYPE: DNA
<213> ORGANISM: Artificial Sequence
<220> FEATURE:
<223> OTHER INFORMATION: Synthetic Oligodeoxyribonucleotide

<400> SEQUENCE: 2
aacgttgtcg tcgacgtcgt cgtcaggcct gacgttatcg atggcgttgt cgtcaacgtt     60
gtcgttaacg tt                                                         72

<210> SEQ ID NO 3
<211> LENGTH: 20
<212> TYPE: DNA
<213> ORGANISM: Artificial Sequence
<220> FEATURE:
<223> OTHER INFORMATION: Synthetic Oligodeoxyribonucleotide

<400> SEQUENCE: 3
tccatgacgt tcctgacgtt                                                 20

<210> SEQ ID NO 4
<211> LENGTH: 24
<212> TYPE: DNA
<213> ORGANISM: Artificial Sequence
<220> FEATURE:
<223> OTHER INFORMATION: Synthetic Oligodeoxyribonucleotide

<400> SEQUENCE: 4
tcgtcgtttt gtcgttttgt cgtt                                            24

<210> SEQ ID NO 5
<211> LENGTH: 23
<212> TYPE: DNA
<213> ORGANISM: Artificial Sequence
<220> FEATURE:
<223> OTHER INFORMATION: Synthetic Oligodeoxyribonucleotide

<400> SEQUENCE: 5
tcgacgttcg tcgttcgtcg ttc                                             23

<210> SEQ ID NO 6
<211> LENGTH: 21
<212> TYPE: DNA
<213> ORGANISM: Artificial Sequence
<220> FEATURE:
<223> OTHER INFORMATION: Synthetic Oligodeoxyribonucleotide

<400> SEQUENCE: 6
tcgtcgacgt cgttcgttct c                                               21

<210> SEQ ID NO 7
<211> LENGTH: 20
<212> TYPE: DNA
<213> ORGANISM: Artificial Sequence
<220> FEATURE:
<223> OTHER INFORMATION: Synthetic Oligodeoxyribonucleotide

<400> SEQUENCE: 7
tccatgacgt tcctgatcgt                                                 20

<210> SEQ ID NO 8
<211> LENGTH: 23
<212> TYPE: DNA
<213> ORGANISM: Artificial Sequence
<220> FEATURE:
<223> OTHER INFORMATION: Synthetic Oligodeoxyribonucleotide
```

```
<400> SEQUENCE: 8
tcgtcgtttt gtcgttttgt cgt                                     23

<210> SEQ ID NO 9
<211> LENGTH: 21
<212> TYPE: DNA
<213> ORGANISM: Artificial Sequence
<220> FEATURE:
<223> OTHER INFORMATION: Synthetic Oligodeoxyribonucleotide

<400> SEQUENCE: 9
tgactgtaac gttcgagatg a                                       21
```

NATURAL KILLER CELLS AND METHODS FOR ENHANCING VIABILITY, PROLIFERATION AND CYTOTOXICITY OF SAME FOLLOWING CRYOPRESERVATION

CROSS REFERENCE TO RELATED APPLICATIONS

This application claims priority to U.S. Provisional Application No. 62/097,535 Methods for Enhancing Viability, Proliferation and Cytotoxicity of Natural Killer Cells after Cryopreservation, the entire disclosure of which is incorporated herein by reference in its entirety.

FIELD OF INVENTION

The field of the invention relates to medical use of immune system cells in adoptive transfer procedures. Several immune cells including T cells, B cells and Natural Killer (NK) cells have shown effectiveness in combating disease through both autologous and allogenic transplantation. The present invention relates to increasing the supply of NK cells available for immunotherapy.

BACKGROUND OF THE INVENTION

The human immune system is composed of several tissues that are enriched with white blood cells (WBCs) including bone marrow and lymph nodes. WBCs participate in two layers of immune defense, the innate immune response and the adaptive immune response. The innate immune response is the first line of immune defense and is primarily made up of WBCs from the myeloid lineage including neutrophils, monocytes, eosinophils and basophils. These are early responding cells that stage an initial defense and alert the rest of the immune system of an infection. The second line of immune defense is the adaptive immune system and is primarily made up of WBCs from the lymphoid lineage including B cells and T cells. These cells wait to receive information about the invading pathogen and then mount a targeted response.

Natural Killer (NK) cells are specialized lymphocytes that act in innate immunity. They are critically important in the anti-viral response and patients lacking NK cells have persistent viral infections. NK cells destroy compromised cells by recognizing abnormally low levels of major histocompatibility complex (MHC) I. This capability also makes NK cells potent against tumor cells which similarly lack MHC I markers. NK cells mature in the bone marrow and other lymph tissues then enter circulation in blood. From the blood NK cells seek infected or oncogenic tissues by following a trail of inflammatory cytokines secreted by monocytes and other early responding cells. Exposure of NK cells to cytokines such as interferon (IFN) alpha ($\alpha$), IFN beta ($\beta$), and Interleukin 2, 12, 15, 18 and 21 as well as Tumor Necrosis Factor alpha (TNF a) increases NK cytotoxicity by orders of magnitude (Sivori et al. 2004). Such cytotoxic NK cells respond aggressively by killing infected cells and thereby limiting the spread of infection.

Using lymphocytes for adoptive transfer therapy was first reported over 50 years ago where transplanted T cells conferred immunity to cancer in rodent models (Mitchison 1955). Adoptive T cell transfer involves the isolation of T cells from blood or bone marrow followed by concentration or expansion of the cells in vitro. Once a sufficiently large or concentrated population is obtained the T cells are infused into a patient (Restifo et al. 2006, Kalos et al. 2013). More recently clinicians have sought to use NK cells for adoptive transfer because of their ability to recognize and kill tumor cells without requiring any particular tumor cell marker (Alizadeh et al. 2010). However development of NK cell adoptive transfer procedures has been impeded by the limited supply of viable cells. NK cells represent only a small fraction of the cells in blood and isolation from a typical blood draw does not yield many cells. Furthermore, NK cells must be purified away from contaminating PBMCs such as T and B cells by CD3 and CD19 depletion, respectively (Childs et al. 2013). This is a necessary step for allogenic transplantation where the presence of T and B cells increases risk of graft versus host disease (GVHD) but further reduces the NK cell yield.

In addition, NK cells expand poorly in vitro compared to others kinds of cells due mainly to early senescence (Childs et al. 2013, Denman et al. 2012). Using even the most effective methods, NK cells are susceptible to telomere shortening and senescence after only a few passages (Denmon et al. 2012). The most effective method for increasing NK cell viability and proliferation in vitro is co-culturing with feeder cells. Commonly used feeder cells for NK expansion include irradiated peripheral blood mononuclear cells (PBMCs), Epstein-Barr virus-transformed lymphoblastoid cell lines (EBC-LCL), gene-modified K562 cells constitutively expressing IL-15 or 21, and other irradiated tumor cell lines (Berg et al. 2009, Childs et al. 2013, Baek et al. 2013). Co-culturing with feeder cells significantly increases NK cell viability and proliferation with population increases between 1,000 and 50,000 times (Denman et al. 2012, Childs et al. 2013). Although NK cells grown on feeder cells can be used clinically, feeder cells remain undesirable because of the increased risk of contamination and the need for additional testing for bacteria, endotoxin and mycoplasma contamination (Childs et al. 2013).

NK cells may be cultured without feeder cells if provided with sufficient cytokines such as IL-2, 12, 15, 18, 21 or nicotinamide. The resulting NK cells exhibit increased cytotoxicity compared to freshly isolated NK cells but can only be expanded between 100 and 300 times (Carlens et al. 2001, Childs et al. 2013, Klingeman et al. 2004). The limited expansion potential is due to telomere loss and senescence (Denman et a. 2012). In addition, residual IL-2 can have severe side effects on patients (Ni 2013).

A problem related to the short supply and difficulty of expanding NK cells is the fact that they do not tolerate cryopreservation in liquid nitrogen well (Berg et al. 2009, Childs et al. 2013). The problem is less severe in feeder based systems but remains a serious problem for feeder free systems (Berg et al. 2009). Losses in both viability and cytotoxicity resulting from cryopreservation are only partly rescued by addition of IL-2 to culture media (Childs et al. 2013, Berg et al. 2009). Cryopreservation of NK cells is a clinical necessity for adoptive transfer immunotherapy because without it only cells freshly isolated from patient blood can be used. Fresh NK cells require a patient to be ready for infusion at a very specific time point after isolation and if that time point is missed, something that frequently occurs with ill patients, the entire procedure must be aborted.

What is needed is an increased supply of NK cells cultured in feeder free systems available for adoptive transfer procedures. The supply of NK cells would be greatly expanded by the ability to efficiently cryopreserve and then later expand NK cells in vitro and restore cytotoxicity without feeder cells and without requiring large quantities of cytokines. Such NK cells would be available to patients on a more flexible basis and remove a barrier to adoptive transfer of NK cells.

RELATED ART

The entire contents of all the references (including literature references, issued patents, published patent applications, and co-pending patent applications) cited throughout this application are hereby expressly incorporated by reference.

US 2012/0148553-Methods of Generating Natural Killer Cells: Discloses a method for producing NK cells from hematopoietic stem cells or progenitor cells.

U.S. Pat. No. 8,735,148-Preserved Compositions of Activated NK Cells and Methods of Using the Same: Discloses NK cells that maintain their activated stated after preservation.

US 2012/0269856-Stable Immunogenic Protein Having Multiple Cysteine Molecules Process Therefore and Composition Thereof: Discloses a stable immunogenic protein.

US 2001/0034330-Innate Immunity-Stimulating Compositions of CPG and Saponin and Methods Thereof: CpG dinucleotides are discussed.

US 2004/0132685-Immunostimulatory Nucleic Acid: Discloses novel immunostimulatory nucleic acid composition: Discloses the effects of CpG compositions on the behavior of B cells.

U.S. Pat. No. 6,406,705-Use of Nucleic Acids Containing Unmethylated CPG Dinuculeotide as an Adjuvant: Discusses in vivo administration of CpG dinucleotides with coupling or crosslinking agents to enhance uptake by target immune system cells, B, monocytic, and NK cells.

US 2010/0330101-Bifunctional CPG or Oligo-Polynucleotide and Toxin or Enterotoxin Containing Composition: Discloses a composition of immunostimulatory DNA, including mono, di, oligo or polynucleotides. In combination with an antigen, and in combination with receptor ligand proteins such as cholera toxin, subunit B of CT, *E Coli* toxin U.S. Pat. No. 7,745,598-CpG Single Strand Deoxynucleotides for use as Adjuvant: Discloses using one or more CpG dinculeotides in combination with vaccines, rabies and HBV to improve the immunostimulatory effect.

U.S. Pat. No. 8,017,749-Compositions and Methods to Treat Cancer with Cupredoxins and CpG Rich DNA: Discloses using CpG dinucleotides from bacteria in combination with Cupredoxin and other carrier molecules for treating cancer.

US 2009/0263405-CpG Oligonucleotide Prodrugs, Compositions Thereof and Associated Therapeutic Methods: Discloses using CpG oligonucleotides with a thermo labile substituent, and carrier molecules.

EP 1796652-Stabilization of Alum-Adjuvanted Immunologically Active Agents: Discloses methods and compositions of alum-adjuvanted immunologically active agents. Discusses the effect of freeze-drying, lyophilizing DNA and adjuvanted preparations.

WO/2005/060330-Freeze-dried Vaccine Adjuvant: Discloses adjuvant that can be freeze-dried and then later dissolved without requiring heating.

CN 1307196C-Modified CpG Oligodeoxynucleotide with Improved Immunoregulatory Function. Discloses immunostimulatory CpG sequences, describes their effect on B cell and NK cells, among others.

CN 1271733-No Title Available: Discloses CpG's are a vaccine adjuvant. Describes some CpG nucleotides sequences.

EP 2172216-Use of Nucleic Acids containing unmethylated CpG dinucleotide as an Adjuvant: Discloses in vivo administration of CpG dinucleotides to stimulate NK and other cells. Describes prolonged stimulation by using stabilized DNA.

EP 2575878-Vaccines Comprising Cholesterol and CPG as Sold Adjuvant Carrier Molecules: Discloses the immunostimulatory effect of CpGs on NK cells among others.

WO/2002/069369-CpG-Like Nucleic Acids and Methods of Use Thereof: Discloses unique CpG nucleic acid sequences that are immunostimulatory for NK cells.

EP 1789435-A Method for Production of Mature Natural Killer Cell: Discloses use of a protein ligand that binds to the Ax1 receptor tyrosine kinase to induce differentiation from immature to mature NK cells.

WO/2006/073422-Activation of Natural Killer (NK) cells and Methods of Use: Discloses use of CpG nucleotides for stimulation of NK cells.

REFERENCES CITED

Carlens, S. et al. A new method for in vitro expansion of cytotoxic human CD3-CD56+ natural killer cells Human Immunology, Volume 62, Issue 10, October 2001, Pages 1092-1098.

H.-G. Klingemann, J. Martinson Ex vivo expansion of natural killer cells for clinical applications. Cytotherapy. Volume 6, Issue 1, January 2004, Pages 15-22

Childs, R. W. et al. Bringing natural killer cells to the clinic: ex vivo manipulation. Clinical Production and Applications of Natural Killer Cell Immunotherapy. American Society of Hematology. Hematology 2013.

Alizadeh, D., et al. Induction of anti-glioma NK cell response following multiple lowdose intracerebral CpG therapy. Clin Cancer Res. 2010; 16(13): 3399-3408.

Baek, H J., et al. Ex Vivo Expansion of Natural Killer Cells Using Cryopreserved Irradiated Feeder Cells. Anticancer Res. 2013; 33(5):2011-9.

Ballas, Z. K., et al. Divergent Therapeutic and Immunologic Effects of Oligodeoxynucleotides with Distinct CpG Motifs. J Immunol 2001; 167:4878-4886.

Berg, M., et al. Clinical Grade Ex Vivo-Expanded Human Natural Killer Cells Upregulate Activating Receptors and Death Receptor Ligands and Have Enhanced Cytolytic Activity against Tumor CellsCytotherapy. 2009; 11(3): 341-55.

Denman, C. J., et al. Membrane-Bound IL-21 Promotes Sustained Ex Vivo Proliferation of Human Natural Killer Cells. PLoS ONE 7(1): e30264. doi: 10.1371/journal.pone.0030264

Kalos, M., et al. Adoptive T cell Transfer for Cancer Immunotherapy in the Era of Synthetic Biology. Immunity 2013; 39.

Kranzer, M., et al. CpG-oligodeoxynucleotides enhance T-cell receptor-triggered interferon-production and up-regulation of CD69 via induction of antigen-presenting cell-derived interferon type I and interleukin-12 Immunology. 2000; 99(2): 170-178.

Lapteva, N. et al. Large-scale ex vivo expansion and characterization of natural killer cells for clinical applications. Crit Rev Oncog 2014; 19(1-2):121-132.

Link B K, et al. Oligodeoxynucleotide CpG 7909 Delivered as Intravenous Infusion Demonstrates Immunologic Modulation in Patients With Previously Treated Non-Hodgkin Lymphoma J Immunother 2006; 29: 558-568.

Mitchison, N. A., et al. Studies On The Immunological Response To Foreign Tumor Transplants In The Mouse. J. Exp. Med. 1955; 102, 157-177.

Ni, J., et al. Toward the next generation of NK cell-based adoptive cancer immunotherapy. OncoImmunology 2013; 2:4, e23811.

Poli, A., et al. CD56 bright natural killer (NK) cells: an important NK cell subset. Immunology 2009; 126(4): 458-465.

Gattinoni et al. Adoptive immunotherapy for cancer: building on success. Nat Rev Immunol. 2006; 6(5): 383-393.

Sfondrini, L., et al. Anti-tumor activity of CpG-ODN aerosol in mouse lung Metastases. Int. J. Cancer 2013; 133, 383-394.

Sivori, S., et al. CpG and double-stranded RNA trigger human NK cells by Toll-like receptors: Induction of cytokine release and cytotoxicity against tumors and dendritic cellsProc Natl Acad Sci. 2004; 101(27): 10116-10121.

Sivori, S., et al. Comparison of different CpG oligodeoxynucleotide classes for their capability to stimulate human NK cells. Eur. J. Immunol. 2006. 36: 961-967

Wagner, H. Toll Meets Bacterial CpG-DNA. Immunity 2001; 14: 499-502.

Yang, L., et al. CpG oligodeoxynucleotides with double stem-loops show strong immunostimulatory activity. International Immunopharmacology 2013; 15: 89-96.

SUMMARY OF THE INVENTION

The present invention provides NK cells and improved methods for feeder free culture of NK cells following cryopreservation. The method enables increased viability, proliferation and cytotoxicity of NK cells by culturing thawed cells in the presence of short oligodeoxyribonucleotides (ODNs) bearing a CpG dinucleotide repeat motif. The results disclosed herein demonstrate that when NK cells thawed following cryopreservation are cultured without feeder cells in the presence of CpG ODNs they exhibit increased viability, proliferation and cytotoxicity compared to control cells cultured without CpG ODNs.

In one aspect of the present invention, NK cells thawed following cryopreservation and cultured without feeder cells in the presence of CpG ODNs have increased viability compared to cells cultured without CpG ODNs. In a non-limiting example, cellular viability is optionally assayed by trypan blue staining and quantification of the exclusion ratio.

In another aspect of the present invention, NK cells thawed following cryopreservation and cultured without feeder cells in the presence of CpG ODNs have increased proliferation compared to cells cultured without CpG ODNs. In a non-limiting example, cellular proliferation is optionally assayed by cell counter and quantification of the starting and ending NK cell population size.

In another aspect of the present invention, NK cells thawed following cryopreservation and cultured without feeder cells in the presence of CpG ODNs have increased cytotoxicity compared to cells cultured without CpG ODNs. In a non-limiting example, NK cell cytotoxicity is optionally assayed by mixing cytotoxic NK cells with K562 lysis target cells and quantification of lysed cells by CYTOTOX 96.

Non-limiting examples of CpG ODNs that may optionally be used according to the method include one or a mixture chosen from the group consisting of:

SEQ ID NOs: 1.

In another embodiment of the present invention, NK cells thawed following cryopreservation and cultured without feeder cells in the presence of CpG ODNs and additionally cultured in the presence of cytokines exhibit additional increases in viability, proliferation and cytotoxicity compared to only CpG ODN supplementation and compared to control cells with no ODN or cytokine supplementation.

Non-limiting examples of cytokines that may optionally be used according to the method include one or a mixture chosen from the group consisting of: IL-2, IL-12, IL-15, IL-18, IL-21, IFNα, IFNβ, TNFα.

A further object of the present invention is to provide NK cells thawed following cryopreservation and cultured without feeder cells in the presence of CpG ODNs that exhibit increased viability, proliferation, and cytotoxicity without requiring large quantities of cytokines.

A further object of the present invention is to provide NK cells thawed following cryopreservation and cultured without feeder cells in the presence of CpG ODNs that exhibit increased viability, proliferation and cytotoxicity to patients on a flexible basis.

The present invention achieves its objects by providing methods for culturing NK cells thawed following cryopreservation that greatly increases their viability, proliferation, and cytotoxicity. The manners in which the invention achieves its objects and other objects which are inherent in the invention will become more readily apparent when reference is made to the accompanying drawings.

BRIEF DESCRIPTION OF THE DRAWINGS

The above and other objects and features of the present invention will become apparent from the following description of the invention, when taken in conjunction with the accompanying drawings wherein.

DETAILED DESCRIPTION OF THE INVENTION

In the following examples, Human NK cells were isolated from peripheral blood mononuclear cells (PBMCs) of three donors (Samples A, B and C). In other embodiments NK cells from bone marrow, umbilical cord, or other tissues could be used. After in vitro propagation for 2.5 to 3.5 weeks, the cells were frozen and stored in liquid nitrogen. After 3-5 months of cryostorage the cells were thawed and used in the following experiments. In other embodiments longer periods of cryopreservation could be used.

CpG ODNs are short single-stranded synthetic DNA molecules that contain a cytosine deoxyribonucleotide ("C") followed by a guanine deoxyribonucleotide ("G"). The CpG dinucleotide motifs (CpGs) function as pathogen-associated molecular patterns (PAMPs) due to their abundance in microbial genomes and rarity in vertebrate genomes (Wagner 2001). CpG ODNs are typically in the range of 8 to 40 base pairs in length but may optionally be longer or shorter. NK cells recognize and bind to the ODNs through the Toll-Like Receptors (TLR), including TLR 9 (TLR9) which is a highly conserved gene that acts to recognize PAMPs (Sivori 2004). CpG ODN signaling via TLR9 stimulates NK cells to increase expression of a host of factors indicative of activation and cytotoxicity, IFNγ and TNFα among others (Sivori et al. 2004, 2006)

In the following examples the CpG ODN used was D-SL03, SEQ ID NO: 1, a 29-mer deoxyribo-oligonucleotide and full phosphorothioate modification. In other embodiments other ODN sequences could be used. D-SL03 belongs to Class C CpG ODN-multispecies, has a double stem loop and contains unmethylated CpGs dinucleotides in a sequence context that is recognized by TLR9. In other embodiments others classes of CpG ODNs could be used including class A or B. In still another embodiment the CpG ODN used can be a mixture of sequences. In yet another embodiment, nucleic acids of any size (even many kb long) can be used since larger nucleic acids are degraded into oligonucleotides within cells.

NK cells thawed from liquid nitrogen cryopreservation were counted using an automated cell counter. The trypan blue exclusion assay was used to determination of the proportion of viable NK cells. NK cellular proliferation was determined by cell comparing starting and ending cell counts. Cytotoxicity of NK cells was determined using CYTOTOX 96 Non-Radioactive Cytotoxicity Assay Kit from Promega when a 10:1 ratio of NK cells to K562 target cells was used.

EXAMPLES

The present invention is illustrated by the following Examples which in no way should be construed as further limiting. The entire contents of all the references (including literature references, issued patents, published patent applications, and co-pending patent applications) cited throughout this application are hereby expressly incorporated by reference.

Example 1: D-SL03 Alone Increases Viability and Proliferation Rate of NK Cells (Sample A) after Cryopreservation Sample A ($1\times10^6$ cells/ml, viability 89.7% immediately after thawing) was exposed to different concentrations of D-SL03 24 hours after thawing for 24 and 48 hours.

Figure 1:
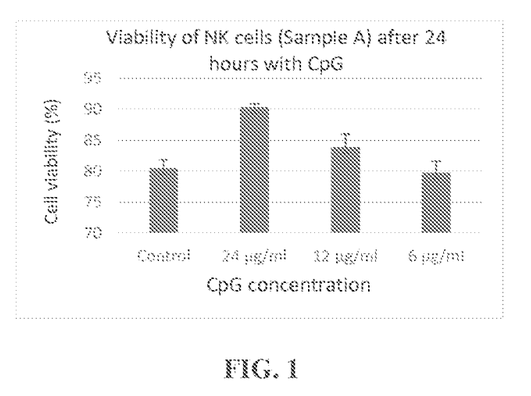
FIG. 1 is a graph showing average cell viability for populations of NK cells (Sample A) 48 hours post thaw, cultured for 24 hours in the presence of CpG ODN.

FIG. 1 shows the average viability of cells 48 hours post thaw, and after 24 hours of treatment with D-SL03. The viability of control cells decreased to an average of 80.5%, down from 89.7% at thaw. The viability of cells treated with 24 ug/ml of D-SL03, was 90.3%, or 12.2% greater than that of control cells. The viability of cells treated with 12 ug/ml of D-SL03 was 4% greater than the viability of control cells. The viability of cells treated with 6 ug/ml of D-SL03 showed no increase in viability compared to control cells after 24 hours.

Figure 2:
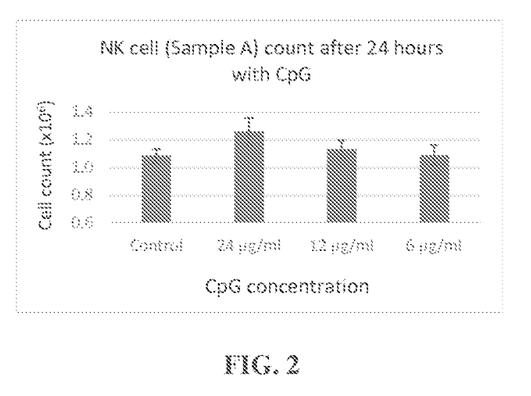
FIG. 2 is a graph showing average cell count/ml for populations of NK cells (Sample A) 48 hours post thaw, cultured for 24 hours in the presence of CpG ODN.

FIG. 2 shows the average number of NK cells/ml 48 hours post thaw and after 24 hours of treatment with D-SL03. The average number of control cells per/ml 48 hours post thaw was 1.08e6 cells/ml. This represents a statistically non-significant increase from the plating number after 24 hours of 1.06e6 cells/ml on the first day. The average number of cells after treatment with 24 ug/ml of D-SL03, was 1.26e6 cells/ml, or 16.7% greater than that of control cells. The average number of cells/ml after treatment with 12 ug/ml of D-SL03 was 4.6% greater (statistically non-significant) than the average number of control cells. The average number of cells after treatment with 6 ug/ml of D-SL03 was 1% greater (statistically non-significant) than that of control cells after 24 hours.

Figure 3:
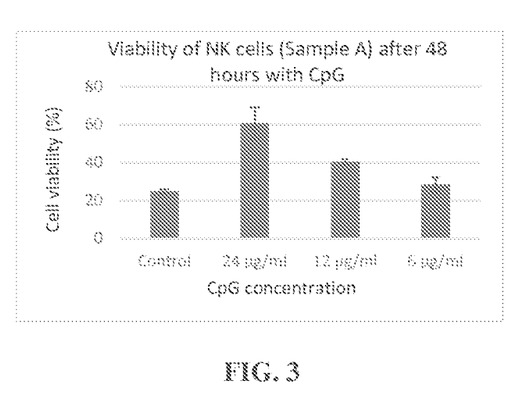
FIG. 3 is a graph showing average cell viability for populations of NK cells (Sample A) 72 hours post thaw, cultured for 48 hours in the presence of CpG ODN.

FIG. 3 shows the average cell viability of the cells 72 hours post thaw, and after 48 hours of treatment with D-SL03. The viability of cells treated with 24 ug/ml of D-SL03, was 143% greater than that of control cells. The viability of cells treated with 12 ug/ml of D-SL03 was 62% greater than the viability of control cells. The viability of cells treated with 6 ug/ml of D-SL03 was 13% greater than the viability of control cells after 48 hours.

Figure 4:
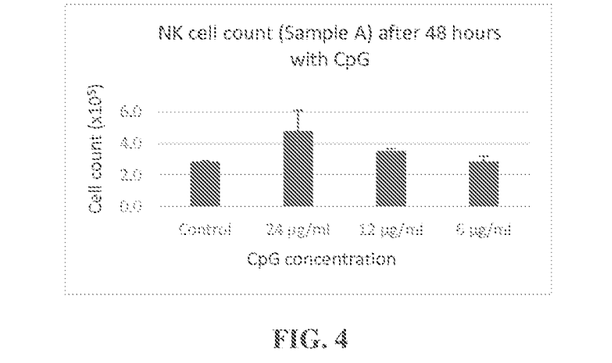
FIG. 4 is a graph showing average cell count/ml for populations of NK cells (Sample A) 72 hours post thaw, cultured for 48 hours in the presence of CpG ODN.

FIG. 4 shows the average number of cells/ml 72 hours post thaw and after 48 hours of treatment with D-SL03. The average number of cells/ml after treatment with 24 ug/ml of D-SL03, was 68% greater than that of control cells. The average number of cells after treatment with 12 ug/ml of D-SL03 was 23.5% greater than the average number of control cells. The average number of cells after treatment with 6 ug/ml of D-SL03 showed no increase over control cells after 48 hours.

These results show that in the absence of CpGs post-thawing, NK cells are prone to low viability and progressive reduction in population size. The results demonstrate that in the presence of D-SL03, NK cell viability after cryopreservation can be increased by as much as 12% after 24 hours and up to 143% after 48 hours compared with control untreated cells. The results also show that the cell population can contain 68% more cells after 48 hours in the presence of D-SL03 versus control cells. These results show the potency of CpG ODN, D-SL03 in particular, to boost NK cell viability following cryopreservation. Based on the data for Sample A, it was concluded that CpG ODN should be applied immediately after thawing to maintain higher cell count and viability. Hence, subsequent experiments were carried out with D-SL03 added to NK cells immediately after thawing.

Example 2: D-SL03 Alone Increases Viability, Proliferation Rate, and Cytotoxicity of NK Cells (Sample B) after Cryopreservation Sample B ($2\times10^6$ cells/ml, viability 89.5% immediately after thawing) was exposed to different concentrations of D-SL03 immediately after thawing for 48 hours.

Figure 5:
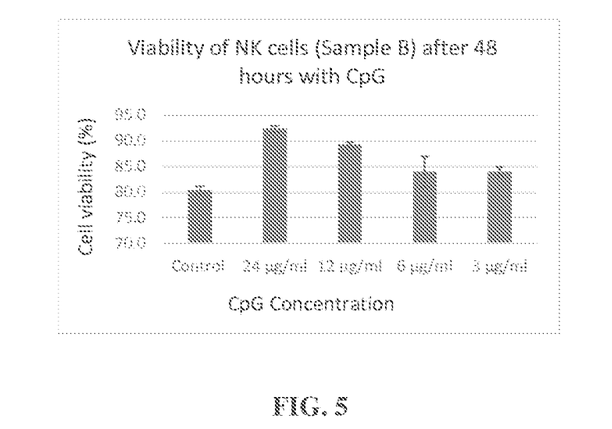
FIG. 5 is a graph showing the average NK cell viability (Sample B) of the cells 48 hours post thaw, cultured for 48 hours in the presence of CpG ODN.

FIG. 5 shows that the viability of control untreated cells after 48 hours in culture decreased to an average of 80.4%, compared at 89.5% after 48 at thaw. The viability of cells treated with 24 ug/ml D-SL03, was 92.4% on average (14.9% increase), 89.3% at 12 ug/ml (11.0% increase) and 84% for both 6 ug/ml and 3 ug/ml of D-SL03, statistically non-significant increase compared with control cells.

Figure 6:
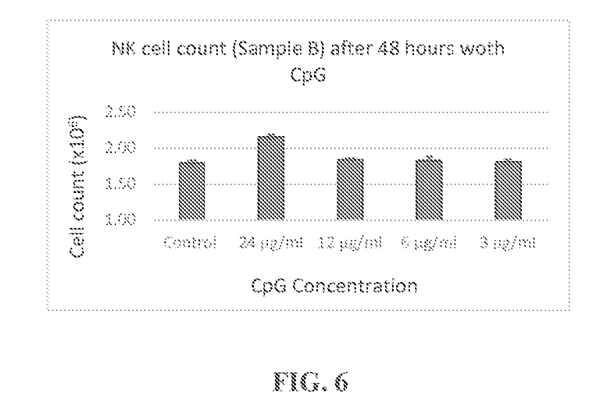
FIG. 6 is a graph showing average cell count/ml for populations of NK cells (Sample B) 48 hours post thaw, cultured for 48 hours in the presence of CpG ODN.

FIG. 6 shows the average number of NK cells/ml 48 hours post thaw and incubation with D-SL03. The population sizes of cells treated with 24, 12, 6, and 3 µg/ml of D-SL03 were 20%, 2.8%, 1.7% and 0.6% greater, with the last 3 numbers being statistically non-significant compared with control cells.

Figure 7:
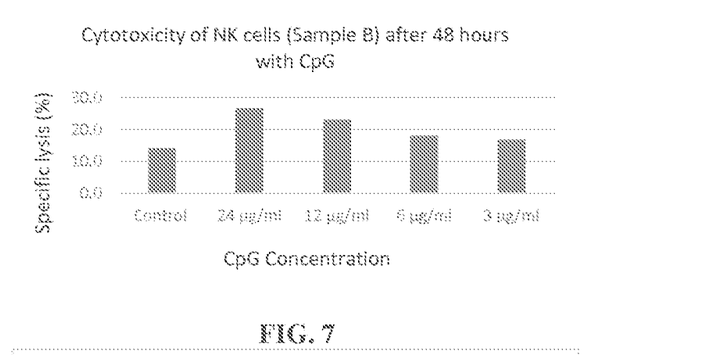
FIG. 7 is a graph showing cytotoxicity for populations of NK cells (Sample B) expressed as specific lysis of target cells by NK cells 48 hours post thaw, cultured for 48 hours in the presence of CpG ODN.

FIG. 7 shows increase in cytotoxicity NK of cells 48 hours post thaw and incubation with D-SL03. The cytotoxicity of NK cells expressed as specific lysis of target cells by NK cells treated with 24, 12, 6, and 3 µg/ml of D-SL03 was 88.7%, 62.6%, 28.2%, and 19.0%, respectively, greater than that of control cells.

The results presented for Sample B where NK cells were incubated with D-SL03 starting immediately after thaw and continuing for 48 hours show that there was no statistically significant drop in viability of control cells as with sample A. Nevertheless, incubation with D-SL03 resulted in statistically significant increase in viability at 24 and 12 µg/ml of D-SL03. A 20% increase in proliferation rate for D-SL03 at 24 µg/ml was also observed. In addition to increased viability and population size, D-SL03 also increased cytotoxicity of NK cells by as much as 88.7% at 24 µg/ml compared with control cells.

Example 3: D-SL03 Plus IL-12 Further Increases Viability, Proliferation Rate, and Cytotoxicity of NK Cells (Sample C) after Cryopreservation Sample C ($2\times10^6$ cells/ml, viability 75.9% immediately after thawing) was exposed to different concentrations of D-SL03 and 1 µg/ml of IL-12 immediately after thawing for 48 hours. Control cells were propagated in the presence of 1 µg/ml of IL-12.

Figure 8:
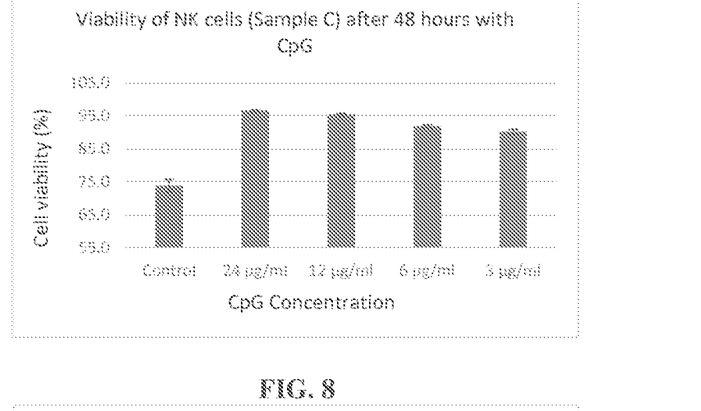
FIG. 8 is a graph showing the average NK cell viability (Sample C) of the cells 48 hours post thaw, cultured for 48 hours in the presence of CpG ODN and IL-12.

FIG. 8 shows that the viability of control cells after 48 hours in culture with immediate after thawing exposure to IL-12 decreased to an average of 73.9%, compared with 75.9% (statistically non-significant decrease) at 48 hours after thawing. The viability of cells treated with 24, 12, 6 and 3 µg/ml of D-SL03, was 30.6%, 28.8%, 24.2%, and 22.0% greater than that of control cells.

Figure 9:
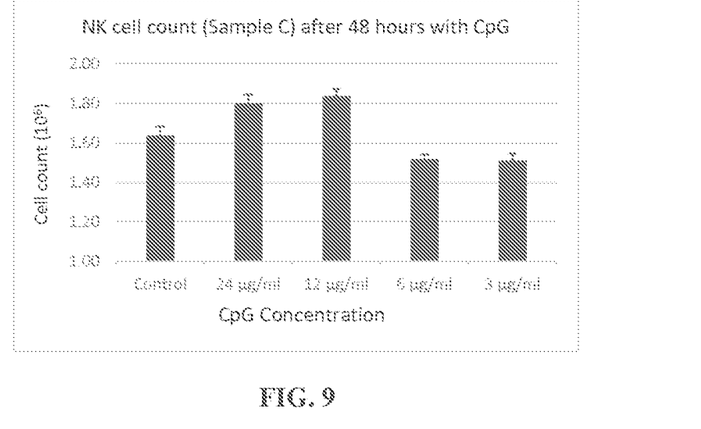
FIG. 9 is a graph showing average cell count/ml for populations of NK cells (Sample C) 48 hours post thaw, cultured for 24 hours in the presence of CpG ODN and IL-12.

FIG. 9 shows the average number of NK cells/ml 48 hours post thaw and incubation with D-SL03 and IL-12. The population sizes of cells treated with 24, 12, 6, and 3 µg/ml of D-SL03 were 9.8%, 12.2%, greater and there was no statistically significant change, respectively, compared with control cells.

Figure 10:
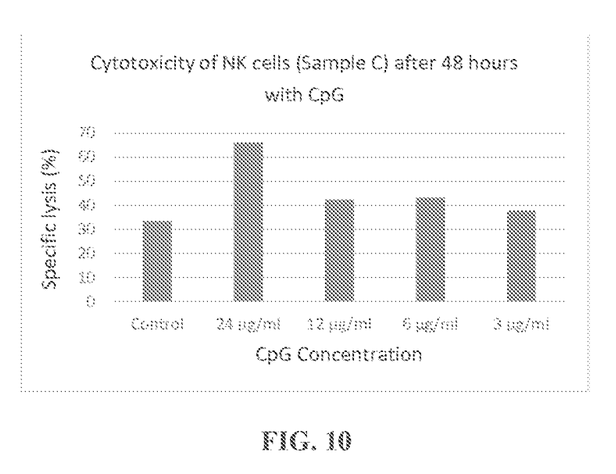
FIG. 10 is a graph showing cytotoxicity for populations of NK cells (Sample C) expressed as specific lysis of target cells by NK cells 48 hours post thaw, cultured for 48 hours in the presence of CpG ODN and IL-12.

FIG. 10 shows increase in cytotoxicity NK of cells 48 hours post thaw and incubation with D-SL03 and IL-12. The cytotoxicity of NK cells expressed as specific lysis of target cells by NK cells treated with 24, 12, 6, and 3 µg/ml of D-SL03 was 97.3%, 26.3%, 28.6%, and 12.8%, respectively, greater than that of control cells. The results presented show that, IL-12 together with D-SL03, has a synergistic effect on NK cell viability compared with Sample B, 30.6% vs 14.9%, but does not boost proliferation. Synergism is also noted for cytotoxicity, 97.3% vs 88.7% without IL-12.

The results with NK cells in Sample C indicate that D-SL03 is a potent booster of NK cell viability, proliferation rate and cytotoxicity in thawed NK cells compared to cells that were not treated with D-SL03. CpG ODN should be added to NK cells immediately after thawing. IL-12 acts synergistically with D-SL03 in terms of increasing NK cell viability and cytotoxicity.

It will be understood that various modifications can be made to the various embodiments of the present invention herein disclosed without departing from the spirit and scope thereof. Therefore, the above description should not be construed as limiting the invention, but merely as an exemplification of preferred embodiments thereof. Those of skill in the art will envision other modifications within the scope and sprit of the present invention as defined by the claims appended hereto.

EQUIVALENTS

Those skilled in the art will recognize, or be able to ascertain using no more than routine experimentation, many equivalents of the specific embodiments of the invention described herein. Such equivalents are intended to be encompassed by the following claims.

What is claimed is:

1. A feeder free method of increasing viability, proliferation and cytotoxicity of isolated natural killer (NK) cells following cryopreservation comprising:
   a. Isolating peripheral blood mononuclear cells (PBMCs) from blood;
   b. Expanding NK cells from said PBMCs in a feeder free system;
   c. Cryopreserving said expanded NK cells;
   d. Thawing said cryopreserved NK cells;
   e. Culturing said thawed NK cells in a feeder free system;
   f. Adding a supplement to said feeder free system comprising a CpG oligodeoxyribonucleotide (ODN) identical to SEQ ID NO: 1 immediately after thawing.

2. The method of claim 1 further comprising adding IL-12 at a concentration of 1 ug/ml to said feeder free system immediately after thawing.

3. The method of claim 1 further consisting of adding cytokines to said feeder free system immediately after thawing.

4. The method of claim 2 further comprising adding CpG ODN identical to SEQ ID NO: 1 at a concentration of 3 ug/ml to 24 ug/ml.

5. A feeder free method of increasing viability, proliferation and cytotoxicity of isolated NK cells following cryopreservation comprising:
   a. Expanding NK cells from PBMCs in a feeder free system;
   b. Cryopreserving said expanded NK cells;
   c. Thawing said cryopreserved NK cells;
   d. Culturing said thawed NK cells in a feeder free system;
   e. Adding a supplement to said feeder free system comprising a CpG ODN identical to SEQ ID NO: 1 after thawing.

6. The method of claim 5 further comprising adding IL-12 at 1 ug/ml to said feeder free system after thawing.

7. The method of claim 5 further consisting of adding cytokines to said feeder free system after thawing.

8. The method of claim 6 further comprising adding CpG ODN identical to SEQ ID NO: 1 at a concentration of 3 ug/ml to 24 ug/ml.

9. A feeder free method of increasing viability, proliferation and cytotoxicity of isolated NK cells following cryopreservation comprising:
   a. Cryopreserving NK cells expanded in a feeder free system;
   b. Thawing said cryopreserved NK cells;
   c. Culturing said thawed NK cells in a feeder free system;
   d. Adding a supplement to said feeder free system, immediately after thawing, comprising CpG ODN that functions as a pathogen-associated molecular pattern.

10. The method of claim 9 further comprising adding IL-12 at a concentration of 1 ug/ml to said feeder free system immediately after thawing.

11. The method of claim 9 further consisting of adding cytokines to said feeder free system immediately after thawing.

12. The method of claim 10 further comprising adding CpG ODN that functions as a pathogen-associated molecular pattern at a concentration of 3 ug/ml to 24 ug/ml.

13. A feeder free method of increasing viability, proliferation and cytotoxicity of isolated NK cells following cryopreservation comprising:
   a. Cryopreserving NK cells expanded in a feeder free system;
   b. Thawing said cryopreserved NK cells;
   c. Culturing said thawed NK cells in a feeder free system;
   d. Adding a supplement to said feeder free system, after thawing, comprising a CpG ODN that functions as a pathogen-associated molecular pattern.

14. The method of claim 13 further comprising adding IL-12 at a concentration of 1 ug/ml to said feeder free system after thawing.

15. The method of claim 13 further consisting of adding cytokines to said feeder free system after thawing.

16. The method of claim 14 further comprising adding CpG ODN that functions as a pathogen-associated molecular pattern at a concentration of 3 ug/ml to 24 ug/ml.

* * * * *